United States Patent
Ansorge et al.

(10) Patent No.: US 7,227,045 B2
(45) Date of Patent: Jun. 5, 2007

(54) PROCESS FOR THE PREPARATION OF LINEAR OLEFINS AND USE THEREOF TO PREPARE LINEAR ALCOHOLS

(75) Inventors: Joachim Ansorge, The Hague (NL); Hendrik Dirkzwager, Amsterdam (NL); Joannes Ignatius Geijsel, The Hague (NL); Abdul Razak Mohamad Ali, Amsterdam (NL); Timothy Michael Nisbet, Amsterdam (NL); Laurent Alain Michel Fenouil, Twickenham (GB)

(73) Assignee: Shell Oil Company, Houston, TX (US)

( * ) Notice: Subject to any disclaimer, the term of this patent is extended or adjusted under 35 U.S.C. 154(b) by 237 days.

(21) Appl. No.: 10/842,403

(22) Filed: May 10, 2004

(65) Prior Publication Data

US 2004/0209964 A1  Oct. 21, 2004

Related U.S. Application Data

(62) Division of application No. 10/153,955, filed on May 23, 2002, now Pat. No. 6,770,191.

(30) Foreign Application Priority Data

May 25, 2001  (EP)  .................................. 01304650

(51) Int. Cl.
| | |
|---|---|
| *C07C 45/00* | (2006.01) |
| *C07C 27/00* | (2006.01) |
| *C07C 1/00* | (2006.01) |
| *C10G 51/02* | (2006.01) |
| *C10G 47/00* | (2006.01) |

(52) U.S. Cl. ...................... 568/451; 568/454; 518/700; 585/324; 208/67; 208/108

(58) Field of Classification Search .................. 208/67, 208/108, 107; 518/700; 585/324; 568/454, 568/451
See application file for complete search history.

(56) References Cited

U.S. PATENT DOCUMENTS

| 4,469,895 | A | * | 9/1984 | Knifton et al. .............. 568/454 |
| 4,579,986 | A | | 4/1986 | Sie ............................. 585/324 |
| 4,619,757 | A | | 10/1986 | Zimmermann ............... 108/57 |
| 6,051,743 | A | | 4/2000 | Bahrmann et al. .......... 568/882 |
| 6,497,812 | B1 | | 12/2002 | Schinski ..................... 208/131 |
| 6,756,411 | B2 | | 6/2004 | Betts et al. ................. 518/701 |

FOREIGN PATENT DOCUMENTS

| EP | 0584879 A1 | 8/1993 |
| WO | WO 97/01521 | 1/1997 |

* cited by examiner

*Primary Examiner*—J. Parsa

(57) ABSTRACT

Process for the preparation of a mixture comprising $C_5+$ linear olefins, which process comprises the steps of
(a) reacting carbon monoxide and hydrogen in the presence of an effective amount of Fischer-Tropsch catalyst under Fischer-Tropsch reaction conditions;
(b) separating from the hydrocarbon mixture thus prepared at least one hydrocarbon fraction, of which at least 95% by weight consists of hydrocarbons containing 15 carbon atoms or more;
(c) contacting this hydrocarbon fraction with hydrogen in the presence of an effective amount of hydrogenation catalyst under hydrogenation conditions;
(d) subjecting the hydrogenated hydrocarbon fraction thus obtained to a mild thermal cracking treatment; and
(e) separating from the cracked product thus prepared the mixture comprising $C_5+$ linear olefins.

22 Claims, 1 Drawing Sheet

PROCESS FOR THE PREPARATION OF LINEAR OLEFINS AND USE THEREOF TO PREPARE LINEAR ALCOHOLS

This is a division of application Ser. No. 10/153,955 filed May 23, 2002, now U.S. Pat. No. 6,770,191, the entire disclosure of which is hereby incorporated by reference.

The present invention relates to a process for the preparation of linear olefins and to a process to prepare linear alcohols from an olefin-containing feed, which is at least partly based on these linear olefins.

BACKGROUND OF THE INVENTION

There are various methods known in the art to prepare linear olefins.

Such process is disclosed in U.S. Pat. No. 4,579,986. This U.S. patent discloses a process for the preparation of linear $C_{10}$–$C_{20}$ olefins, which process comprises preparing a mixture of hydrocarbons substantially consisting of linear paraffins by:
 (a) contacting a mixture of carbon monoxide and hydrogen at elevated temperature and pressure with a cobalt-containing catalyst,
 (b) separating from the paraffin mixture thus prepared a heavy fraction which consists substantially of $C_{20}$+ paraffins, and
 (c) converting at least this heavy fraction (a "wax") by mild thermal cracking into a mixture of hydrocarbons which consists substantially of linear olefins and contains the desired $C_{10}$–$C_{20}$ olefins.

Although the wax cracking method according to U.S. Pat. No. 4,579,986 performs satisfactorily, there is still room for improvement. Particularly if the starting point is to produce an olefin-containing feed which can be used as (part of) the feedstock for a hydroformylation reaction stage to produce linear detergent and plasticizer alcohols, the method according to U.S. Pat. No. 4,579,986 can be improved. Namely, linear plasticizer alcohols typically contain from 7 to 11 carbon atoms, while linear detergent alcohols typically contain 12 to 15 carbon atoms. Accordingly, any hydrocarbon fraction produced to serve at least partly as the source of hydroformylation feedstocks should contain a significant portion of $C_6$ to $C_{14}$ olefins, at least 80% by weight, but preferably at least 85% by weight, of which consists of the corresponding linear α-olefins. It was found that by hydrogenating the wax feed prior to subjecting it to the mild thermal cracking treatment very high quality $C_6$ to $C_{10}$ and $C_{11}$ to $C_{14}$ linear α-olefins are produced: the $C_6$ to $C_{14}$ olefins produced (contained in a mixture of $C_5$+ olefins) consist for more than 80% by weight of $C_6$ to $C_{14}$ linear α-olefins.

SUMMARY OF THE INVENTION

A process for the preparation of a mixture comprising $C_5$+ linear olefins, which process comprises the steps of
 (a) reacting carbon monoxide and hydrogen in the presence of a Fischer-Tropsch catalyst under Fischer-Tropsch reaction conditions thereby producing a hydrocarbon mixture;
 (b) separating, from the hydrocarbon mixture, at least one hydrocarbon fraction, of which at least 95% by weight consists of hydrocarbons containing 15 carbon atoms or more;
 (c) contacting the thus-separated hydrocarbon fraction with hydrogen in the presence of a hydrogenation catalyst under hydrogenation conditions thereby producing a hydrogenated hydrocarbon fraction;
 (d) subjecting said hydrogenated hydrocarbon fraction to a mild thermal cracking treatment thereby producing a cracked product; and
 (e) separating, from the cracked product, a mixture comprising $C_5$+ linear olefins.

DETAILED DESCRIPTION OF THE INVENTION

Figure 1:
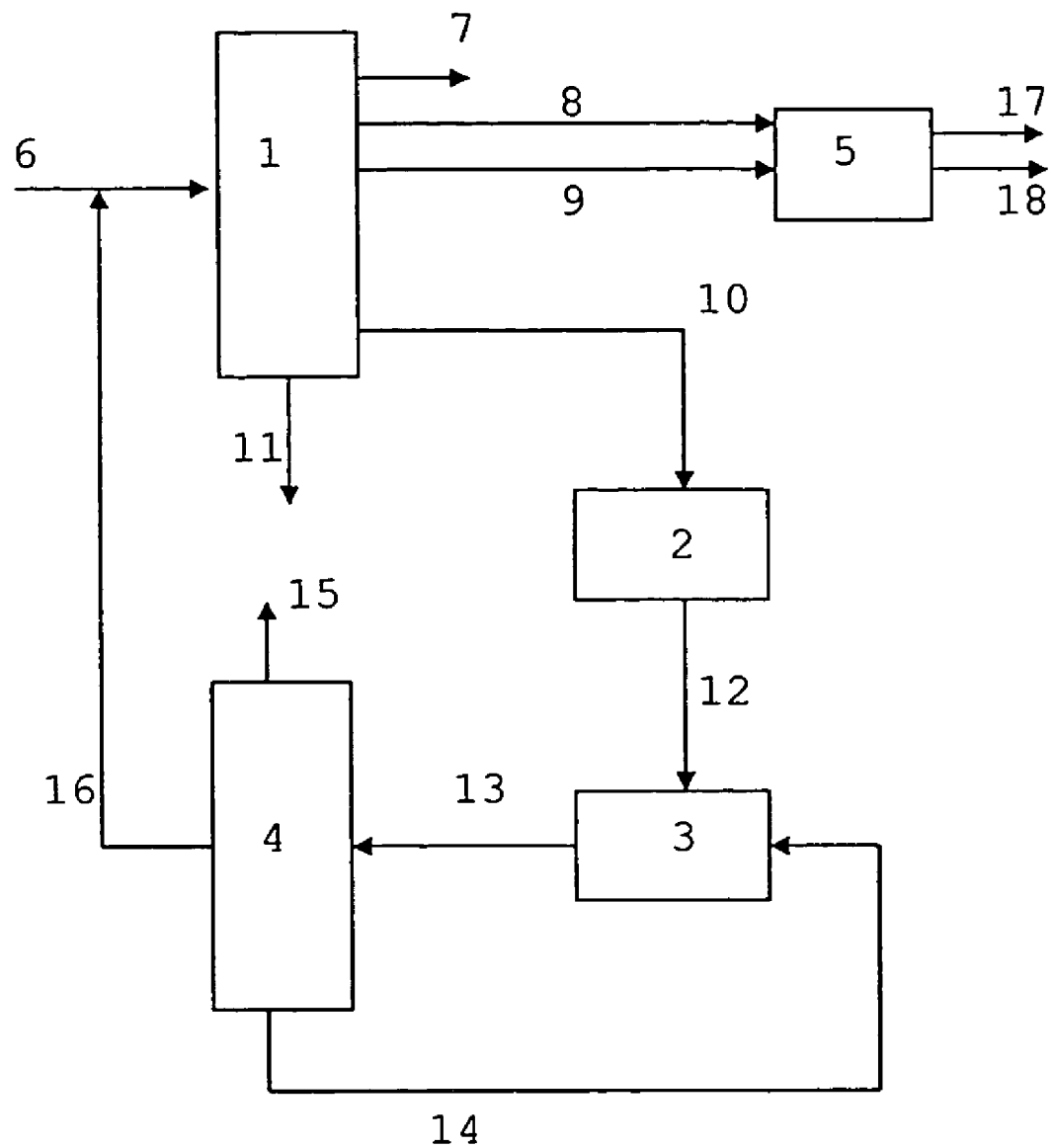
FIG. 1 shows a simplified flow scheme of an exemplary process according to the second aspect of the present invention.

The present invention relates to the preparation of linear olefins by a process which also involves a Fischer-Tropsch hydrocarbon synthesis reaction.

Accordingly, in a first aspect the present invention relates to a process for the preparation of a mixture comprising $C_5$+ linear olefins, which process comprises the steps of
 (a) reacting carbon monoxide and hydrogen in the presence of an effective amount of Fischer-Tropsch catalyst under Fischer-Tropsch reaction conditions;
 (b) separating from the hydrocarbon mixture thus prepared at least one hydrocarbon fraction, of which at least 95% by weight consists of hydrocarbons containing 15 carbon atoms or more;
 (c) contacting this hydrocarbon fraction with hydrogen in the presence of an effective amount of hydrogenation catalyst under hydrogenation conditions;
 (d) subjecting the hydrogenated hydrocarbon fraction thus obtained to a mild thermal cracking treatment; and
 (e) separating from the cracked product thus prepared the mixture comprising $C_5$+ linear olefins.

The product mixture comprising $C_5$+ linear olefins preferably is a mixture comprising $C_5$ to $C_m$ linear olefins with m being an integer of from 10 to 20, preferably 12 to 18, more preferably 12 to 15. A very useful mixture is a mixture comprising $C_5$ to $C_{14}$ linear olefins. Such mixture suitably comprises at least 20% by weight, and more preferably from 25 to 50% by weight, of $C_{11}$ to $C_{14}$ linear α-olefins. The $C_5$ to $C_{10}$ linear α-olefins typically constitute up to 75% by weight of the stream, suitably from 40 to 75% by weight. The balance up to 100% by weight, which forms a relatively small proportion of the stream, consists of hydrocarbons other than the olefins mentioned, such as $C_4$ hydrocarbons and the corresponding $C_5$+ linear alkanes, iso-alkanes, iso-olefins, internal olefins and dienes. Typically this small proportion of other hydrocarbons will not exceed 20% by weight and suitably is less than 10% by weight.

In step (a) of the present process hydrocarbons are formed by reacting carbon monoxide and hydrogen under suitable conditions. In general, the preparation of hydrocarbons from a mixture of carbon monoxide and hydrogen at elevated temperature and pressure in the presence of an effective amount of a suitable catalyst is known as the Fischer-Tropsch hydrocarbon synthesis. Catalysts used in this hydrocarbon synthesis are normally referred to as Fischer-Tropsch catalysts and usually comprise one or more metals from Groups 8, 9 and 10 of the Periodic Table of Elements, optionally together with one or more promoters, and a carrier material. In particular, iron, nickel, cobalt and ruthenium are well known catalytically active metals for such catalyst. The Fischer-Tropsch catalyst to be used in step (a)

of the present process suitably comprises a porous carrier, in particular a refractory oxide carrier. Examples of suitable refractory oxide carriers include alumina, silica, titania, zirconia or mixtures thereof, such as silica-alumina or physical mixtures such as silica and titania. Very suitable carriers are those comprising titania, zirconia or mixtures thereof. Titania carriers are preferred, in particular titania which has been prepared in the absence of sulphur-containing compounds. This carrier may further comprise up to 50% by weight of another refractory oxide, typically silica or alumina. More preferably, the additional refractory oxide, if present, comprises up to 20% by weight, even more preferably up to 10% by weight, of the carrier.

The preferred catalytically active metal is cobalt, although nickel, iron and ruthenium could also be used. The amount of catalytically active metal present in the catalyst may vary widely. Typically, the catalyst comprises 1–100 parts by weight of such metal per 100 parts by weight of carrier, preferably, 3–60 parts by weight, more preferably, 5–40 parts by weight. The above amounts of catalytically active metal refer to the total amount of metal in element form and can be determined by known elemental analysis techniques. For the sake of convenience cobalt is referred to hereinafter as the catalytically active metal, but it is emphasized that instead of or in addition to cobalt other catalytically active metals as mentioned hereinbefore may also be used.

In addition to cobalt the catalyst may comprise one or more promoters known to those skilled in the art. Suitable promoters include manganese, zirconium, titanium, ruthenium, platinum, vanadium, palladium and/or rhenium. The amount of promoter, if present, is typically between 0.1 and 150 parts by weight, for example between 1 and 50 parts by weight, per 100 parts by weight of carrier.

Typically, the Fischer-Tropsch catalyst does not contain alkali or alkaline earth metals, apart from possible impurities introduced with starting materials in the preparation process of the catalysts of the present invention. Typically, the atomic ratio of alkali or alkaline earth metals to cobalt metal is less than 0.01, preferably, less than 0.005.

The Fischer-Tropsch process conditions applied in step (a) of the present process typically include a temperature in the range from 125 to 350° C., preferably 150 to 275° C., and a pressure in the range from 5 to 150 bar abs (bara). Step (a) of the present process may be operated at the pressures conventionally applied, i.e. up to 80 bara, suitably up to 50 bara, but also higher pressures can be applied.

In a preferred embodiment of the present invention step (a) comprises reacting carbon monoxide with hydrogen at a temperature in the range of from 125 to 350° C. and a pressure in the range from 5 to 150 bara in the presence of a catalyst comprising cobalt on a carrier comprising titania. Suitably, the catalyst and process conditions in step (a) are selected such that the product obtained in this step (a) comprises in the range of from 2 to 20% by weight of a $C_{11}$ to $C_{14}$ hydrocarbon fraction, which hydrocarbon fraction comprises in the range of from 10 to 60% by weight based on total weight of this fraction of $C_{11}$ to $C_{14}$ mono-olefins. This could, for instance, be achieved by using a Fischer-Tropsch catalyst based on cobalt and titania at operating temperatures of 175 to 275° C. and operating pressures of 20 to 80 bara.

Hydrogen and carbon monoxide (synthesis gas) are typically fed to the process at an atomic ratio in the range from 0.5 to 4, especially from 1 to 3. In a preferred embodiment, the hydrogen to carbon monoxide atomic ratio is in the range from 1.5 to 2.5.

The Fischer-Tropsch reaction step (a) may be conducted using a variety of reactor types and reaction regimes, for example a fixed bed regime, a slurry phase regime or an ebullating bed regime. It will be appreciated that the size of the catalyst particles may vary depending on the reaction regime they are intended for. It is within the normal skills of the skilled person to select the most appropriate catalyst particle size for a given reaction regime.

Further, it will be understood that the skilled person is capable to select the most appropriate conditions for a specific reactor configuration and reaction regime. For example, the preferred gas hourly space velocity may depend upon the type of reaction regime that is being applied. Thus, if it is desired to operate the hydrocarbon synthesis process with a fixed bed regime, preferably the gas hourly space velocity (GHSV) is chosen in the range from 500 to 2500 Nl/l/h. If it is desired to operate the hydrocarbon synthesis process with a slurry phase regime, preferably the gas hourly space velocity is chosen in the range from 1500 to 7500 Nl/l/h.

In step (b) of the present process at least one hydrocarbon fraction, of which at least 95% by weight, preferably at least 98% by weight, consists of hydrocarbons containing 15 carbon atoms or more (further: $C_{15}+$ fraction), is separated from the hydrocarbon mixture prepared in the preceding Fischer-Tropsch hydrocarbon synthesis step (a). The separation can be performed by methods known in the art. Preferably such separation involves a distillation treatment, notably fractional distillation. Conventional distillation techniques can be used.

The separation in step (b) may be effected solely by distillation, but could also comprise a combination of fractional distillation with another separation treatment, such as stripping or condensing. For instance, the hydrocarbon product from step (a) could also first be separated into a liquid stream and a gaseous stream by passing the hydrocarbon product from step (a) through a condenser, which is suitably operated at similar temperature and pressure conditions as applied in step (a). The liquid stream from the condenser can then be recovered as the $C_{15}+$ fraction, while the gaseous hydrocarbon stream contains the bulk of the hydrocarbons with lower carbon numbers (typically up to $C_{14}$). The gaseous stream is subsequently liquefied and subjected to a fractional distillation treatment to recover the desired hydrocarbon fractions for further treatment.

The $C_{15}+$ fraction will not normally contain more than 5% by weight, suitably not more than 2% by weight, of hydrocarbons containing more than n carbon atoms with n as defined hereinafter. The $C_{15}+$ fraction used as the feed to step (c) may be the $C_{15}+$ fraction as such, but may also be a $C_{15}-C_n$ fraction with n being an integer of at least 18, preferably at least 20, and at most 40, preferably at most 35, more preferably at most 30. The upper limit is suitably selected such that the feed to the wax cracking step (d) is completely gaseous under the cracking conditions in order to avoid coke formation in the wax cracker. The remaining heavy $C_n+$ fraction could also be, in whole or in part, used as a feed to step (c) of the present process or subjected to other treatments, such as heavy paraffin cracking treatment which results in oil products like naphtha, kerosine and gasoil. The expression "$C_{15}+$ fraction" as used hereinafter will also include the $C_{15}-C_n$ fraction as defined above.

In step (c) hydrogenation of the $C_{15}+$ fraction takes place. The hydrogenation treatment is typically carried out in the presence of a hydrogenation catalyst and hydrogen at a temperature from 100 to 400° C., preferably from 100 to 300° C., more preferably, 150 to 275° C., even more preferably 180 to 250° C. Typically, a hydrogen partial pressure is applied in the range from 10 to 250 bara, preferably from 10 to 150 bara, more preferably from 10 to 50 bara, even more preferably from 15 to 45 bara. Hydrogen may be supplied to the hydrogenation treatment stage at a gas hourly space velocity in the range of from 100 to 10000 Nl/l reaction zone volume/hr, more preferably from 250 to 5000 Nl/l reaction zone volume/hr. The $C_{15}+$ fraction being treated is typically supplied to the hydrogenation treatment stage at a weight hourly space velocity in the range of from 0.1 to 5 kg/l reaction zone volume/hr, more preferably from 0.25 to 2.5 kg/l reaction zone/hr. The ratio of hydrogen to $C_{15}+$ fraction may range from 100 to 5000 Nl/kg and is preferably from 250 to 3000 Nl/kg.

Hydrogenation catalysts are known to those skilled in the art and are available commercially, or may be prepared by methods well known in the art. Typically, the hydrogenation catalyst comprises as catalytically active component one or more metals selected from Groups 6, 8, 9 and 10 of the Periodic Table of Elements, in particular one or more metals selected from molybdenum, tungsten, cobalt, nickel, ruthenium, iridium, osmium, platinum and palladium. Preferably, the catalyst comprises one or more metals selected from nickel, platinum and palladium as the catalytically active component. A particularly suitable catalyst comprises nickel as a catalytically active component.

Catalysts for use in the hydrogenation treatment stage typically comprise a refractory metal oxide or silicate as a carrier. Suitable carrier materials include silica, alumina, silica-alumina, zirconia, titania and mixtures thereof. Preferred carrier materials for inclusion in the catalyst for use in the process of this invention are silica, alumina, silica-alumina, and diatomaceous earth (kieselguhr).

The catalyst may comprise the catalytically active component in an amount of from 0.05 to 80 parts by weight calculated as element, preferably from 0.1 to 70 parts by weight, per 100 parts by weight of carrier material. The amount of catalytically active metal present in the catalyst will vary according to the specific metal concerned. One particularly suitable catalyst for use in the hydrogenation treatment stage comprises nickel in an amount in the range of from 30 to 70 parts by weight (calculated as element) per 100 parts by weight of carrier material. A second particularly suitable catalyst comprises platinum in an amount in the range of from 0.05 to 2.0 parts by weight per 100 parts by weight of carrier material.

In subsequent step (d) mild thermal cracking of the hydrogenated hydrocarbon fraction obtained in step (c) takes place. This mild thermal cracking can be carried out by ways known in the art. In one preferred embodiment the mild thermal cracking step (d) is carried out in the presence of steam. Such treatment is, for instance, described in the aforementioned U.S. Pat. No. 4,579,986, which is incorporated by reference herein. A suitable mild thermal cracking treatment involves cracking the hydrogenated hydrocarbon fraction at a temperature of from 450 to 675° C., preferably 480 to 600° C., a pressure of from 1 to 50 bara, preferably 1 to 10 bara and more preferably 1 to 5 bara, and a residence time of 0.5 to 20 seconds, preferably 1 to 10 seconds. The thermal cracking can be carried out with or without diluent. Suitable diluents include steam and inert gases, of which steam is preferred. If used, steam is typically used in an amount of up to 40% by weight (based on hydrocarbon feed), preferably 3 to 30% by weight. As indicated, an inert gas may also be used as diluent. An inert gas in this connection is a gas, which does not interfere with the cracking reactions by decomposition and/or reacting with the hydrocarbon reactants and cracking products. Examples of suitable inert gases include nitrogen and noble gases like helium and argon. It was found that using a diluent has a positive impact on the amount of by-products formed.

In a preferred embodiment the mild thermal cracking treatment comprises the stages of:

(d1) combining the diluent and the hydrogenated hydrocarbon fraction in an evaporator, and (d2) thermally cracking the evaporated hydrocarbon fraction.

The evaporator is usually operated at a temperature sufficiently high to evaporate the hydrogenated hydrocarbon stream. This will normally be at least 350° C., suitably at least 400° C., while the maximum temperature will usually not exceed 600° C., suitably 500° C., in order to avoid excessive cracking. The actual cracking in stage (d2) typically takes place at a temperature of from 450 to 650° C., suitably 480 to 600° C., a pressure of at least 1 bara and usually not more than 300 bara, suitably from 1 to 10 bara, more suitably 1 to 5 bara, a residence time of 0.5 to 20 seconds, suitably 1 to 10 seconds in the presence of the diluent.

As will be discussed hereinafter, subsequent separation step (e) may yield a heavy $C_m+$ hydrocarbon stream, which can be at least partly recycled to cracking step (d), either directly or via hydrogenation step (c). In such mode of operation thermal cracking step (d) is suitably carried out under such conditions that the conversion of hydrocarbons per pass is in the range of from 10 to 50% by weight, preferably 10 to 35% by weight and more preferably 15 to 30% by weight, based on total weight of hydrocarbons passed through the thermal cracking reactor in that pass.

In subsequent step (e) the desired mixture comprising the $C_5+$ linear olefins is separated from the cracked product. In principle any separation technique suitable for separating the $C_5+$ hydrocarbon mixture from the cracked product can be used. This could involve short path distillation techniques like separation with a wiped film evaporator, stripping techniques and fractional distillation at atmospheric or reduced pressure. For the purpose of the present invention one particularly suitable separation method comprises the stages of:

(e1) cooling the cracked product and separating from the cooled cracked product the liquid cracked product containing the $C_5+$ hydrocarbons, and (e2) separating from the liquid cracked product the mixture comprising the $C_5-C_m$ linear olefins.

Typically cooling and first separation stage (e1) take place in a gas/liquid separator. The hot cracked product is first cooled to a temperature at which the desired $C_5+$ hydrocarbons become liquid and the gaseous $C_1$ to $C_4$ products as well as any diluent used in the cracking treatment can be removed as gases. It will be understood that a small amount of $C_5+$ hydrocarbons will end up in the gaseous stream, while a small portion of the $C_4$-hydrocarbons will end up in the liquid stream. It will be appreciated that the exact temperature applied depends on the pressure applied. The liquid stream recovered from the gas/liquid separator contains the desired $C_5+$ hydrocarbons and is fed to subsequent separation stage (e2), where the $C_5-C_m$ hydrocarbon stream containing the mixture of $C_5-C_m$ linear olefins is separated. This stage can suitably be conducted in a stripper, optionally using a stripping gas like steam, nitrogen, helium or argon. The $C_5-C_m$ hydrocarbon stream containing the mixture of $C_5-C_m$ linear olefins is recovered as the top fraction. In a further separation stage (e3) the $C_m+$ bottom fraction is suitably at least partly recycled to hydrogenation step (c) and/or to cracking step (d).

The mixture comprising $C_5+$ linear olefins as obtained by the process described hereinbefore typically comprises from 20 to 50% by weight of $C_{11}$ to $C_{14}$ linear α-olefins and from 40 to 75% by weight of $C_5$ to $C_{10}$ linear α-olefins and hence is a very suitable feedstock for preparing linear detergent and plasticizer alcohols in a hydroformylation reaction.

Accordingly, in a second aspect the present invention relates to a process for the preparation of linear alcohols by reacting an olefin-containing feed with carbon monoxide and hydrogen in the presence of an effective amount of hydroformylation catalyst under hydroformylation conditions, wherein the olefin-containing feed is at least partly based on the mixture comprising $C_5+$ linear olefins obtained by the process as described hereinbefore.

A very suitable process in this connection is a process, wherein the olefin-containing feed is obtained by subjecting to a fractionation treatment:
(a) a first hydrocarbon stream derived from reacting carbon monoxide and hydrogen in the presence of an effective amount of Fischer-Tropsch catalyst under Fischer-Tropsch reaction conditions, and
(b) a second hydrocarbon stream consisting of the mixture comprising $C_5+$ linear olefins obtained by the process as described hereinbefore.

The weight ratio of the first hydrocarbon stream to the second hydrocarbon stream may vary within broad limits, but suitably is in the range of from 0.1:1 to 30:1, preferably 1:1 to 30:1 and more preferably 5:1 to 25:1.

The fractionation treatment suitably corresponds with separation step (b) of the process according to the first aspect of the present invention as described hereinbefore.

The first hydrocarbon stream is the product of a Fischer-Tropsch hydrocarbon synthesis reaction, suitably the entire $C_4+$ product recovered from a Fischer-Tropsch hydrocarbon synthesis reaction. This reaction, its conditions and ways of operation have been extensively discussed hereinbefore. Suitably, the first hydrocarbon stream comprises from 2 to 20% by weight, more suitably 3 to 10% by weight, of $C_{11}$ to $C_{14}$ hydrocarbons. Of these $C_{11}$ to $C_{14}$ hydrocarbons 10 to 60% by weight, suitably 15 to 50% by weight, consists of $C_{11}$ to $C_{14}$ linear mono-olefins.

The second hydrocarbon stream consists for at least 95% by weight, preferably at least 98% by weight, of hydrocarbons comprising 5 or more carbon atoms and typically comprises from 20 to 50% by weight of $C_{11}$ to $C_{14}$ linear α-olefins, while levels of 30% by weight or more and even 35% by weight or more are also achievable. The amount of $C_5$ to $C_{10}$ linear α-olefins in the second hydrocarbon stream typically ranges from 40 to 75% by weight. The balance up to 100% by weight consists of hydrocarbons other than the olefins mentioned, such as $C_4$ hydrocarbons and the corresponding $C_5+$ linear alkanes, iso-alkanes, iso-olefins, internal olefins and dienes.

FIG. 1 shows a simplified flow scheme of an exemplary process according to the second aspect of the present invention.

In this FIG. 1 a Fischer-Tropsch $C_4+$ hydrocarbon product stream 6 obtained in a Fischer-Tropsch hydrocarbon synthesis process (not shown) is passed into fractionation column 1. A $C_4$–$C_5$ fraction 7, a $C_6$–$C_{10}$ fraction 8, a $C_{11}$–$C_{14}$ fraction 9, a $C_{15}$–$C_{30}$ fraction 10 and a $C_{30}+$ fraction 11 are recovered. The $C_6$–$C_{10}$ fraction 8 and the $C_{11}$–$C_{14}$ fraction 9 are passed into hydroformylation unit 5, where they are converted into respectively plasticizer alcohols 17 and detergent alcohols 18. The $C_{30}+$ fraction 11 can be passed into a heavy paraffin cracker (not shown) to be converted in e.g. middle distillates like naphtha and kerosine. The $C_{15\text{-}30}$ fraction 10 is passed into hydrogenation unit 2, resulting in hydrogenated fraction 12, which is subsequently cracked in mild thermal cracking unit 3. The cracked product 13 is fed to fractionation unit 4, from which a $C_4$-fraction 15, a $C_5$–$C_{14}$ fraction 16 and a $C_{15}+$ fraction 14 are recovered. The latter is recycled to cracking unit 3, while the $C_5$–$C_{14}$ fraction 16 is combined with Fischer-Tropsch $C_4+$ hydrocarbon product stream 6 and passed into fractionation column 1.

The invention is further illustrated by the following examples without limiting the invention to these specific embodiments.

EXAMPLE 1

Two commercially available hydrogenated Fischer-Tropsch reactor products (available under the trade marks SX-30 and SX-50) were combined in a weight ratio SX-50:SX-30 of 70:30 and subsequently 5% by weight (based on the total weight of SX-30 plus SX-50) of hexadecane was added in order to simulate a hydrogenated $C_{16}+$ Fischer-Tropsch feed for the wax cracker. The composition of this feed is shown in Table 1.

TABLE 1

Feed compositions

| C-fraction | after hydrogenation (% by weight) |
|---|---|
| $C_{14}$– paraffin | 0.0 |
| $C_{15}$–$C_{20}$ paraffin | 32.9 |
| $C_{21}$–$C_{25}$ paraffin | 26.4 |
| $C_{26}$–$C_{30}$ paraffin | 35.3 |
| $C_{31}+$ paraffin | 5.4 |

For the actual cracking reaction a AISI 310 reactor tube (length 30 cm, volume 10 ml) was used. Accordingly, the hydrogenated fraction was subsequently combined at a feed rate of 12 grams per hour with recycled $C_{15}$–$C_{20}$ fraction recovered from the cracked product at a recycle ratio (i.e. weight ratio of recycled fraction to fresh hydrogenated fraction) of 3.2. The combined paraffinic stream was dosed at 70° C. from a heated storage vessel into an evaporator where it was combined with helium at a mole ratio helium to hydrocarbon of 1. The temperature in the evaporator was approximately 400° C. The evaporated stream was subsequently passed into the cracking zone where cracking took place at a temperature of 560° C. and a pressure of 3 bara at a residence time of 4 seconds. The cracked product was subsequently separated into a gaseous fraction (helium and $C_1$–$C_4$ hydrocarbons), a liquid cracked product $C_5$–$C_{14}$ fraction and a liquid $C_{15}$–$C_{20}$ product, which was recycled to be combined with freshly hydrogenated feed prior to entering the evaporator. The composition of the cracked product $C_1$–$C_{14}$ is indicated in Table 2.

TABLE 2

Composition of cracked product

| Fraction | Weight %[1] | Mono-olefin | Weight %[1] |
|---|---|---|---|
| $C_1$–$C_4$ (par + olef) | 37 | $C_{11}$–$C_{12}$ | 9.7 |
| $C_5$–$C_{14}$ (par + olef) | 63 | $C_{13}$–$C_{14}$ | 9.2 |

[1] based on total weight of $C_1$–$C_{14}$ formed

EXAMPLE 2

The liquid cracked product $C_5$–$C_{14}$ fraction obtained in Example 1 was fractionated using a 15 tray packed Fischer packed distillation column at a reflux ratio of 25. The $C_{11}/C_{12}$ fraction and the $C_{13}/C_{14}$ fraction obtained through this fractionation were subjected to a hydroformylation treatment to produce the corresponding alcohols. The compositions of the both fractions are given in Table 3.

Hydroformylation of both fractions was carried by charging a 1.5 liter autoclave with 565 grams of feedstock consisting of 53% by weight of the $C_{11}/C_{12}$ fraction or the $C_{13}/C_{14}$ fraction, 34% by weight of iso-octane (as diluent), 1% by weight of n-decane or tetradecane (as internal standard for respectively the $C_{11}/C_{12}$ fraction and the $C_{13}/C_{14}$ fraction) and 12% by weight of 2-ethylhexanol in which KOH and the hydroformylation catalyst were dissolved. The hydroformylation catalyst was based on cobalt octanoate as cobalt precursor and 9-eicosyl-9-phosphabicyclononane as the ligand and these were added in such amount that the amount of catalyst was 0.25% by weight based on total feedstock added and the ligand/cobalt molar ratio was 1.2. The amount of KOH present in the 2-ethylhexanol was such that the K/Co molar ratio amounted to 0.4. Hydroformylation was subsequently carried out at 192° C. and 70 bara synthesis gas ($H_2$/CO molar ratio=2). The reaction time was 3 hours. The conversion achieved was >98.5%.

The crude alcohol products obtained were successively subjected to a single stage evaporative distillation (Rotavap operation at 100 mbara and bath temperature of 80–220° C.), saponification through the addition of $NaHB_4$ at 50–90° C., two water washing treatments at 80–90° C. to remove the inorganic salts formed and a distillative treatment at reduced pressure to remove the light and heavy products ("topping and tailing" treatment).

The composition of the alcohol products thus obtained is indicated in Table 3.

TABLE 3

Hydroformylation of cracked product

| C-fraction | Cracked $C_{11/12}$ (% w) | Alcohol $C_{12/13}$ (% w) | Cracked $C_{13/14}$ (% w) | Alcohol $C_{14/15}$ (% w) |
|---|---|---|---|---|
| C10 | | | | |
| alkenes (all) | 3.3 | | | |
| n-alkane | <0.1 | | | |
| linear alcohol | | <0.1 | | |
| C11 | | | | |
| 1-alkene | 43.9 | | | |
| other alkenes[1] | 3.9 | | | |
| n-alkane | 0.2 | <0.1 | | |
| linear alcohol | | <0.1 | | <0.1 |
| C12 | | | | |
| 1-alkene | 40.5 | | 1.0 | |
| other alkenes[1] | 4.6 | | 0.3 | |
| n-alkane | 1.6 | <0.1 | <0.1 | <0.1 |
| linear alcohol | | 41.3 | | <0.1 |
| branched alcohol | | 7.1 | | |
| C13 | | | | |
| 1-alkene | 1.0 | | 44.5 | |
| other alkenes[1] | 0.7 | | 4.7 | |
| n-alkane | 0.2 | | 1.4 | <0.1 |
| linear alcohol | | 34.4 | | 0.8 |
| branched alcohol | | 16.0 | | |
| C14 | | | | |
| 1-alkene | | | 40.3 | |
| other alkenes[1] | | | 4.5 | |
| n-alkane | | | 1.4 | <0.1 |
| linear alcohol | | | | 42.2 |
| branched alcohol | | 0.9 | | 13.3 |
| C15 | | | | |
| 1-alkene | | | 0.7 | |
| other alkenes[1] | | | 0.5 | |
| n-alkane | | | 0.2 | <0.1 |
| linear alcohol | | | | 30.4 |
| branched alcohol | | | | 12.3 |
| C16 | | | | |
| branched alcohol | | | | 0.8 |

[1]other alkenes include dienes, branched alkenes and internal alkenes

We claim:

1. A process for the preparation of linear alcohols by reacting an olefin-containing feed with carbon monoxide and hydrogen in the presence of a hydroformylation catalyst under hydroformylation conditions, wherein the olefin-containing feed is at least partly based on the mixture comprising $C_5$+ linear olefins produced by a process comprising the steps of
    (a) reacting carbon monoxide and hydrogen in the presence of a Fischer-Tropsch catalyst under Fischer-Tropsch reaction conditions thereby producing a hydrocarbon mixture;
    (b) separating, from the hydrocarbon mixture, at least one hydrocarbon fraction, of which at least 95% by weight consists of hydrocarbons containing 15 carbon atoms or more;
    (c) contacting the thus-separated hydrocarbon fraction with hydrogen in the presence of a hydrogenation catalyst under hydrogenation conditions thereby producing a hydrogenated hydrocarbon fraction;
    (d) subjecting said hydrogenated hydrocarbon fraction to a mild thermal cracking treatment thereby producing a cracked product; and
    (e) separating, from the cracked product, a mixture comprising $C_5$+ linear olefins.

2. The process of claim 1 wherein the olefin-containing feed is obtained by subjecting to a fractionation treatment:
    (a) a first hydrocarbon stream produced from reacting carbon monoxide and hydrogen in the presence of a Fischer-tropsch catalyst under Fischer-Tropsch reaction conditions, and
    (b) a second hydrocarbon stream consisting of the mixture comprising $C_5$+ linear olefins.

3. The process of claim 2 wherein the weight ratio of the first hydrocarbon stream to the second hydrocarbon stream is in the range of from 0.1:1 to 30:1.

4. The process of claim 2 wherein the first hydrocarbon stream comprises from 2 to 20% by weight of $C_{11}$ to $C_{14}$ hydrocarbons, 10 to 60% by weight of which consists of $C_{11}$ to $C_{14}$ linear mono-olefins.

5. A process of claim 2 wherein the second hydrocarbon stream comprises from 20 to 50% by weight of $C_{11}$ to $C_{14}$ linear α-olefins.

6. The process of claim 3 wherein the first hydrocarbon stream comprises from 2 to 20% by weight of $C_{11}$ to $C_{14}$ hydrocarbons, 10 to 60% by weight of which consists of $C_{11}$ to $C_{14}$ linear mono-olefins.

7. The process of claim 1 wherein the mixture comprising $C_5+$ linear olefins is a mixture comprising $C_5$ to $C_m$ linear olefins with m representing an integer of from 10 to 20.

8. The process of claim 7 the olefin-containing feed is obtained by subjecting to a fractionation treatment:
   (a) a first hydrocarbon stream produced from reacting carbon monoxide and hydrogen in the presence of a Fischer-tropsch catalyst under Fischer-Tropsch reaction conditions, and
   (b) a second hydrocarbon stream consisting of the mixture comprising $C_5+$ linear olefins.

9. The process of claim 8 wherein the weight ratio of the first hydrocarbon stream to the second hydrocarbon stream is in the range of from 0.1:1 to 30:1.

10. The process of claim 9 wherein the first hydrocarbon stream comprises from 2 to 20% by weight of $C_{11}$ to $C_{14}$ hydrocarbons, 10 to 60% by weight of which consists of $C_{11}$ to $C_{14}$ linear mono-olefins.

11. The process of claim 9 wherein the second hydrocarbon stream comprises from 20 to 50% by weight of $C_{11}$ to $C_{14}$ linear α-olefins.

12. The process of claim 10 wherein the first hydrocarbon stream comprises from 2 to 20% by weight of $C_{11}$ to $C_{14}$ hydrocarbons, 10 to 60% by weight of which consists of $C_{11}$ to $C_{14}$ linear mono-olefins.

13. The process of claim 1 wherein the mild thermal cracking step (d) is carried out in the presence of a diluent.

14. The process of claim 13 wherein the diluent is steam.

15. The process of claim 7 wherein separation step (e) comprises the steps of:
   (e1) cooling the cracked product and separating from the cooled cracked product the liquid cracked product containing the $C_5+$ hydrocarbons, and
   (e2) separating from the liquid cracked product the mixture comprising the $C_5$–$C_m$ linear olefins.

16. The process of claim 15 wherein the olefin-containing feed is obtained by subjecting to a fractionation treatment:
   (a) a first hydrocarbon stream produced from reacting carbon monoxide and hydrogen in the presence of a Fischer-tropsch catalyst under Fischer-Tropsch reaction conditions, and
   (b) a second hydrocarbon stream consisting of the mixture comprising $C_5+$ linear olefins.

17. The process of claim 12 wherein the weight ratio of the first hydrocarbon stream to the second hydrocarbon stream is in the range of from 0.1:1 to 30:1.

18. The process of claim 13 wherein the first hydrocarbon stream comprises from 2 to 20% by weight of $C_{11}$ to $C_{14}$ hydrocarbons, 10 to 60% by weight of which consists of $C_{11}$ to $C_{14}$ linear mono-olefins.

19. The process of claim 13 wherein the second hydrocarbon stream comprises from 20 to 50% by weight of $C_{11}$ to $C_{14}$ linear α-olefins.

20. The process of claim 14 wherein the first hydrocarbon stream comprises from 2 to 20% by weight of $C_{11}$ to $C_{14}$ hydrocarbons, 10 to 60% by weight of which consists of $C_{11}$ to $C_{14}$ linear mono-olefins.

21. The process of claim 15 wherein the separation step (e) comprises a further step:
   (e3) recycling at least part of the $C_m+$ bottom fraction from separation step to cracking step (d) and/or hydrogenation step (c).

22. The process of claim 1 wherein the thermal cracking step (d) is carried out under conditions in a thermal cracking reactor that the conversion of hydrocarbons per pass is in the range of from 10 to 50% by weight based on total weight of hydrocarbons passed through the thermal cracking reactor in that pass.

* * * * *